(12) United States Patent
Chwae et al.

(10) Patent No.: US 9,309,181 B2
(45) Date of Patent: Apr. 12, 2016

(54) METHOD OF PRODUCING UNSATURATED ACID FROM SALT OF HYDROXYCARBOXYLIC ACID

(71) Applicant: Samsung Electronics Co., Ltd., Suwon-si, Gyeonggi-do (KR)

(72) Inventors: Jun Chwae, Seoul (KR); Hyeon su Heo, Uijeongbu-si (KR); Seung joon Hwang, Seoul (KR); Nam soo Park, Suwon-si (KR); Moo ho Lee, Suwon-si (KR); Kwang myung Cho, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/624,327

(22) Filed: Feb. 17, 2015

(65) Prior Publication Data

US 2015/0232890 A1    Aug. 20, 2015

(30) Foreign Application Priority Data

Feb. 19, 2014    (KR) .................. 10-2014-0019219

(51) Int. Cl.
*C12P 7/40*    (2006.01)
*C07C 57/04*    (2006.01)
*C07C 51/377*    (2006.01)
*C12P 7/42*    (2006.01)

(52) U.S. Cl.
CPC .............. *C07C 57/04* (2013.01); *C07C 51/377* (2013.01); *C12P 7/42* (2013.01)

(58) Field of Classification Search
CPC ........................ C07C 51/377; C07C 57/04
See application file for complete search history.

(56) References Cited

U.S. PATENT DOCUMENTS

| 7,186,856 B2 | 3/2007 | Meng et al. | |
|---|---|---|---|
| 2010/0099910 A1* | 4/2010 | Meng et al. ................ | 562/590 |
| 2011/0118504 A1 | 5/2011 | Haas et al. | |

FOREIGN PATENT DOCUMENTS

| JP | 2010-180171 A | 8/2010 |
|---|---|---|
| JP | 4644119 B2 | 12/2010 |
| JP | 2011-225533 A | 11/2011 |
| KR | 2007-0035562 A | 3/2007 |

OTHER PUBLICATIONS

Database Caplus Chemical Abstracts Service, Columbus, Ohio, US; Database Accession No. 2014:2071660, Abstract of KR 2014140254, Samsung Total Petrochemicals Co., Ltd., S. Korea, Dec. 9, 2014.*
Database Caplus Chemical Abstracts Service, Columbus, Ohio, US; Database Accession No. 2015:133859, Abstract of KR 2015007155, Samsung Total Petrochemicals Co., Ltd., S. Korea, Jan. 20, 2015.*

* cited by examiner

*Primary Examiner* — Karl J Puttlitz
(74) *Attorney, Agent, or Firm* — Leydig, Voit & Mayer, Ltd.

(57) ABSTRACT

A method of producing an unsaturated acid from a salt of a hydroxycarboxylic acid, the method includes providing an aqueous solution including a salt of a hydroxycarboxylic acid; adding a solvent with a boiling point of 200° C. or higher to the aqueous solution; and heating the aqueous solution at a temperature lower than the boiling point of the solvent to split a salt from the salt of the hydroxycarboxylic acid while simultaneously dehydrating the hydroxycarboxylic acid, thereby converting the hydroxycarboxylic acid to the unsaturated acid.

18 Claims, 2 Drawing Sheets

METHOD OF PRODUCING UNSATURATED ACID FROM SALT OF HYDROXYCARBOXYLIC ACID

RELATED APPLICATION

This application claims the benefit of Korean Patent Application No. 10-2014-0019219, filed on Feb. 19, 2014, in the Korean Intellectual Property Office, the disclosure of which is hereby incorporated by reference.

BACKGROUND

1. Field

The present disclosure relates to methods of producing an unsaturated acid from a salt of a hydroxycarboxylic acid.

2. Description of the Related Art

Hydroxycarboxylic acids produced via fermentation may be useful in an industrial process of various purposes, such as synthesizing polyester or polyamide. However, in order to increase productivity of a fermentation process, a neutralizing agent, such as ammonia or calcium hydroxide, needs to be added to neutralize acid produced from the fermentation.

Additionally, in order to collect a hydroxycarboxylic acid present in the fermentation product, a mineral acid, such as sulfuric acid, is conventionally added to the product to perform acid-treatment, and thus ammonium sulfate or gypsum (calcium sulfate) is produced as a by-product.

Thus an additional process and facility for implementing said process are needed to purify fermentation by-products and convert hydroxycarboxylic acid into unsaturated carboxylic acid. Such additional processes raise production costs in part because additional waste generated from the additional process needs to be removed as well.

Therefore, an efficient salt splitting process is needed to effectively use hydroxycarboxylic acid salts in industrial fermentation processes.

SUMMARY

Provided are methods of producing an unsaturated acid from a salt of a hydroxycarboxylic acid by using a cost effective and simple process.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
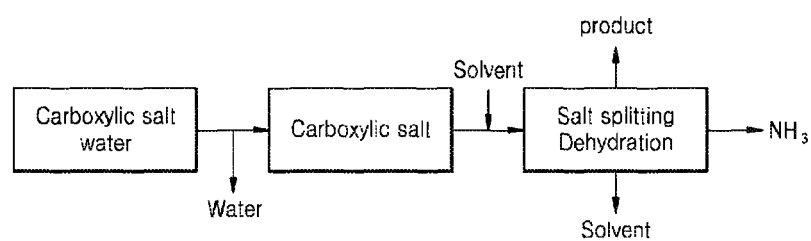
FIG. 1 is a flowchart illustrating a method of producing an unsaturated acid via desalting and dehydration reactions from an aqueous solution of a salt of a carboxylic acid according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, provided is a method of producing an unsaturated acid from an salt of a hydroxycarboxylic acid, the method comprising providing an aqueous solution including a salt of a hydroxycarboxylic acid; adding a solvent with a boiling point of 200° C. or higher to the aqueous solution; and heating the aqueous solution at a temperature lower than the boiling point of the solvent to split the salt of the hydroxycarboxylic acid while simultaneously dehydrating the hydroxycarboxylic acid, thereby converting the hydroxycarboxylic acid to the unsaturated acid.

As used herein the terms "split" and "splitting" refer to the decomposition of a salt into its corresponding acid and base compounds.

The method may include providing an aqueous solution including a salt of a hydroxycarboxylic acid.

The salt of hydroxycarboxylic acid may be an ammonium salt of a hydroxycarboxylic acid. The ammonium salt is ammonia or quaternary ammonium salt. The term "ammonium" may refer to a cation having the formula $NR4^+$ where each R group, independently, is hydrogen or a substituted or unsubstituted alkyl, aryl, aralkyl, or alkoxy group.

The aqueous solution including a salt of a hydroxycarboxylic acid may be derived from a cell culture solution, such as a culture solution that is produced via a fermentation process. The aqueous solution including a salt may be included in the cell culture solution.

The cell culture solution may be cultured by using microorganism or mutated microorganism. The cell culture solution may be produced by using natural microorganism or may be a culture from mutated microorganism for producing desirable products, such as a 3-hydroxypropionic acid (3-HP), an acrylic acid (AA), a 4-hydroxybutanoic acid (4-HB), a lactic acid, or a hydroxycarboxylic acid, as well as an unsaturated acid. The cell culture solution may be from a fermenter or a fermentation solution of microorganism. The microorganism may belong to, for example, a genus of *Escherichia, Enterobacter, Erwinia, Klebsiella, Pantoea, Serratia,* or *Corynebacterium.*

The cell culture solution may be filtered. A culture before concentration may be filtered to split and/or filter strains, proteins, or some mineral salts in the microorganism. The split may be performed by using a centrifuge, a filter press, a press filter, a diatomite filter, a rotary vacuum filter, a membrane separator, or a method of coagulation and floatation.

The aqueous solution including the salt of the hydroxycarboxylic acid may be provided to a batch-oriented or continuous fermenter. The batch-oriented fermentation may be performed by using a standard batch system or a fed-batch system. The standard batch system may be a closed system, in which a medium composition is loaded in an initial stage of fermentation and not artificially replaced during the fermentation. Thus, in the closed system, the medium is inoculated with desired cells in the initial stage of fermentation, and the fermentation is performed without adding additional components to the system. However, the conventional "batch" fermentation includes adding a carbon source as a one-time treatment and periodic controlling of conditional factors, such as pH and oxygen concentration during the fermentation process. In the batch-oriented system, metabolites and biomass compounds continuously change until the fermentation stops. In the batch culture, the cells are controlled to a highly-productive log phase from a static lag phase and lastly changes to a stationary phase, where a rate of proliferation decreases or stops. If the culture is not treated, the cells at the stationary phase may die. The cells in the log phase generally produce most of the final metabolic products or intermediates.

The fed-batch system may be provided by modification of a standard batch system, in which an increased amount of matrix is added when the fermentation is performed. An amount of a matrix in a medium of the fed-batch system may be limited. In the fed-batch system, a substantial matrix concentration may not be easily measured, and thus the concentration may be evaluated based on changes in measurable factors, such as pH and a partial pressure of dissolved oxygen or a discard gas, such as $CO_2$.

Continuous fermentation is an open system, in which a defined fermentation medium is continuously added to a bioreactor, and the same amount of a conditioned medium is simultaneously removed for the process. The continuous fermentation generally maintains a culture at a constantly high density so that the cells may stay in a highly-productive log phase. Also, in the continuous fermentation, one factor or the number of factors affecting cell proliferation or concentrations of the final products may be controlled. For example, a restrictive nutrition material, such as a carbon source, or a level of nitrogen may be maintained at a fixed ratio, while all other variables are enabled to be controlled. In another system, the cell concentration defined by the turbidity of the medium is maintained constant while other factors that affect proliferation are continuously changed.

The hydroxycarboxylic acid may be selected from the group consisting of an alpha hydroxyl carboxylic acid, a beta hydroxycarboxylic acid, a gamma hydroxycarboxylic acid, an epsilon hydroxycarboxylic acid, and a combination thereof. The hydroxycarboxylic acid may include at least one hydroxyl group and at least one of carboxylic acid.

The alpha hydroxyl carboxylic acid may be a lactic acid, a citric acid, a tartaric acid, or a glycolic acid. The beta hydroxycarboxylic acid may be a 3-hydroxypropionic acid, a 3-hydroxybutyric acid, a 3-hydroxyvaleric acid, a 3-hydroxyhexanoic acid, a 3-hydroxyheptanoic acid, or a 3-hydroxyoctanoic acid. The gamma hydroxycarboxylic acid may be a 4-hydroxybutyric acid, 4-hydroxyvaleric acid, or 4-hydroxyhexanoic acid. The epsilon hydroxycarboxylic acid may be a 5-hydroxyvaleric acid or 5-hydroxyhexanoic acid.

The salt of a hydroxyl carboxylic acid may be an ammonium salt of a hydroxyl carboxylic acid as described above. The ammonium salt of a hydroxyl carboxylic acid may be prepared when the fermentation producing the hydroxyl carboxylic acid is performed with a pH adjusting agent such as ammonia water.

The method may include concentrating the aqueous solution, such as by heating the aqueous solution to first temperature to remove the water. The concentrating of the aqueous solution may include removing water from the aqueous solution. About 99 wt % or more of the whole amount of the water in the aqueous solution may be removed by heating the aqueous solution under a reduced pressure in order to concentrate the aqueous solution. When the hydroxycarboxylic acid is converted to an unsaturated acid by dehydration that does not involve first concentrating the aqueous solution, the unsaturated acid and water form an azeotrope, and purification cost is needed to remove the water at a high cost. Also yield loss may be generated in the process of purifying the unsaturated acid. Also, in the concentrating of the aqueous solution, a water-soluble inorganic salt, which is added in the fermentation process, may be precipitated and removed.

The concentrating of the aqueous solution may precede the adding of a solvent with a boiling point of 200° C. or higher.

Also, the concentrating of the aqueous solution may be performed by using a concentrator selected from the group consisting of a centrifugal concentrator, an evaporator, a convective circulation concentrator, a low temperature decompression concentrator, a rotary decompression concentrator, a decompression evaporator, a thin film concentrator, a plate-type concentrator, and a combination thereof.

The method may include providing a solvent with a boiling point of 200° C. or higher. The boiling point of the solvent method is measured at a pressure of about 1 atm.

After the concentrating of the aqueous solution, adding the solvent having a boiling point of about 200° C. or higher may provide a composition that can be heated to a temperature high enough to facilitate simultaneous splitting the salt of the hydroxycarboxylic acid and dehydrating the hydroxycarboxylic acid to convert the hydroxycarboxylic acid to the unsaturated acid. The solvent may include a sulfur-containing compound, a nitrogen-containing compound, or an oxygen-containing compound. The sulfur-containing compound may be Sulfolane. The nitrogen-containing compound may be pyrrolidone. The oxygen-containing compound may be propylene carbonate. The pyrrolidone may be N-methyl-2-pyrrolidone (NMP). A boiling point of the NMP may be in a range of about 202° C. to about 204° C.

The method may include heating the aqueous solution at a temperature lower than the boiling point of the solvent that is sufficient to split the salt of the hydroxycarboxylic acid while simultaneously dehydrating the hydroxycarboxylic acid, thereby converting the hydroxycarboxylic acid to the unsaturated acid.

Also, a temperature to remove the water of aqueous solution may be a first temperature that is lower than the temperature needed to split a salt from the salt of the hydroxycarboxylic acid. The temperature to split a salt from the salt of the hydroxycarboxylic acid may be a second temperature. The method may, optionally, comprise heating the aqueous solution to the second temperature. The second temperature may be lower than the boiling point of the solvent. The second temperature may be, for example, about 5 to about 185° C., about 5 to about 150° C., about 5 to about 100° C., about 5 to about 50° C., about 10 to about 45° C., about 15 to about 40° C., about 20 to about 35° C., or about 25 to about 30° C. lower than the boiling point of the solvent at a given reaction pressure. A third temperature may be higher than the second temperature and lower than the boiling point of the solvent at a given reaction pressure. The method may, optionally, comprise heating the aqueous solution to the third temperature. The third temperature may be about 1 to about 135° C., about 5 to about 100° C., about 10 to about 90° C., about 15 to about 85° C., or about 20 to about 80° C. higher than the second temperature. The third temperature may be about 0.1 to about 50° C., about 1 to about 40° C., about 1 to about 30° C., or about 1 to about 20° C. lower than the boiling point of the solvent at a given reaction pressure. The heating may be performed at the atmospheric pressure or a reduced pressure. When the heating is performed at a reduced pressure and a temperature lower than a certain temperature A at 1 atm, the heating may work the same as if it was performed at the temperature A at 1 atm.

In the heating the aqueous solution at a temperature lower than the boiling point of the solvent to split the salt of the hydroxycarboxylic acid while simultaneously dehydrating the hydroxycarboxylic acid, thereby converting the hydroxycarboxylic acid to the unsaturated acid, 90 mol % or more, for example, 91 mol % or more, 92 mol % or more, 93 mol % or more, 94 mol % or more, 95 mol % or more, or 96 mol % or more of the salt of the hydroxycarboxylic acid may be converted to a hydroxycarboxylic acid, and the hydroxycarboxylic acid conversion may have a yield of about 50 mol % or more, for example, 65 mol % or more, 75 mol % or more, 85 mol % or more, or 95 mol % or more.

The salt splitting may produce by-products, such as ammonia, and the by-products may be separated or removed from the reactor by heating the by-products, applying vacuum, adding an inert gas, such as nitrogen, or a combination thereof. The salt splitting may be performed by a high temperature concentration method, a fraction distillation method, or a combination thereof. Also, the ammonia or amine may be added back to a fermentation reactor or a fermenter.

The method may further include adding a catalyst to promote the dehydration. The catalyst may be an acidic catalyst, such as a mineral acid; a basic catalyst, such as an amine or a metal hydroxide; or a neutral catalyst, such as a calcium phosphate salt, a calcium lactate salt, an aluminum oxide, a silico-dioxide, or a zeolite.

The method may further include purifying the dehydrated product. The purifying may be performed by, for example distillation.

The present invention will be described in further detail with reference to the following examples. These examples are for illustrative purposes only and are not intended to limit the scope of the present invention.

FIG. 1 is a flowchart illustrating a method of producing unsaturated acid via desalting (i.e., salt splitting) and dehydration reactions from an aqueous solution of an salt of a carboxylic acid and water according to an embodiment of the present invention. As shown in FIG. 1, the aqueous solution of the salt of the hydroxycarboxylic acid and water is concentrated to provide a salt of the hydroxycarboxylic acid from which water is removed. Then, the solvent having a boiling point of 200° C. or more is provided as a solvent, and the salt splitting and dehydration are performed at the same time to obtain an unsaturated acid. The product, such as the unsaturated acid, and $NH_3$ may be obtained and purified through distillation in gaseous phase, and the solvent may be maintained as liquid phase to be used again.

Figure 2:
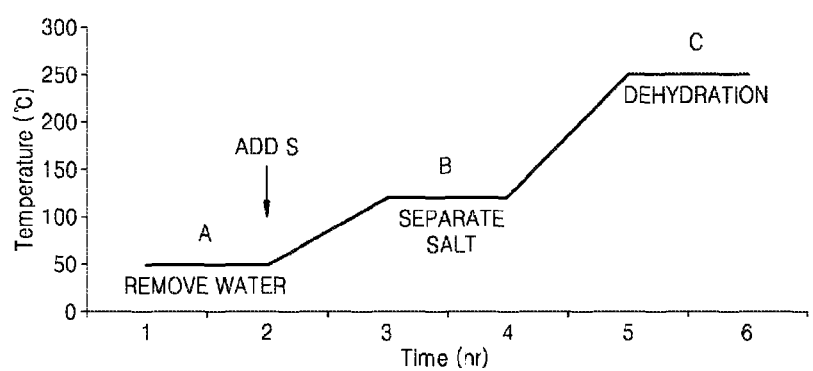
FIG. 2 is graph of temperature plotted against time during a process for the production of acrylic acid from a salt of 3-hydroxypropionic acid by controlling temperature and adding a solvent S in a batch-oriented system.

FIG. 2 is a graphical illustration of a production process of acrylic acid from a salt of 3-hydroxypropionic acid by controlling temperature and adding a solvent S in a batch-oriented system. As shown in FIG. 2, an aqueous solution including a salt of 3-hydroxypropionic acid, that is, after inserting solvent S (e.g., Sulfolane) to a concentrate A, which is prepared by removing water (moisture) from the fermentation solution at a first temperature, the aqueous solution is heated to a second temperature (120° C. at 30 torr) and a third temperature (about 250° C. under a condition of about 300 ml/min of a $N_2$ flow rate), and then a product C distilled out through an upper part of a 3-neck flask is cooled and collected. B denotes 3-hydroxypropionic acid from which the salt from the salt of 3-hydroxypropionic acid is separated.

Figure 3:
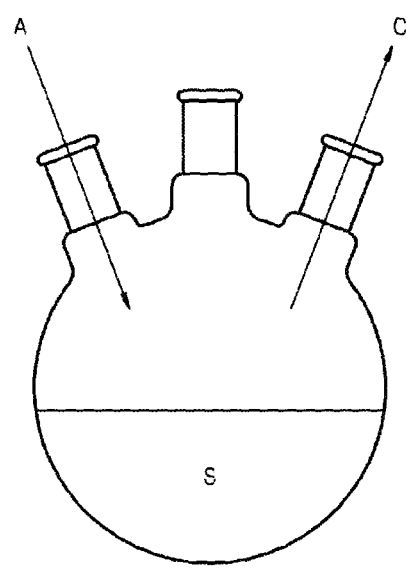
FIG. 3 is a schematic view of a 3-neck flask for producing an unsaturated acid from a salt of a hydroxycarboxylic acid through a continuous process.

FIG. 3 is a schematic of a 3-neck flask for producing unsaturated acid from a salt of a hydroxycarboxylic acid through a continuous process. FIG. 3 illustrates a method of producing an unsaturated acid when the aqueous solution including the salt of the carboxylic acid is provided to a continuous reactor. As shown in FIG. 3, the aqueous solution including the salt of 3-hydroxypropionic acid, that is, the concentrate A, which is prepared by removing water (moisture) from the fermentation solution, is inserted to the 3-neck flask containing the solvent S (e.g., Sulfolane), and thus the product C distilled out through an upper part of the 3-neck flask is cooled and collected.

EXAMPLE 1

Preparation of Acrylic Acid from Ammonium Salt of 3-Hydroxypropionic Acid Included in Fermentation Solution in Batch System 100 g of a fermentation solution including 9.36 wt % of 3-hydroxypropionic acid (3-HP) was added to a 3-neck flask (500 ml), and a temperature of the flask was increased to 50° C. under 30 torr to remove all water in the fermentation solution. Cells in the fermentation solution were removed by performing centrifuge. Then, 200 g of pure Sulfolane was added thereto, and a temperature of the aqueous solution was increased to 120° C. and allowed to react under 30 torr for 1 hour.

The resultant was titrated using KOH to measure a conversion ratio of the ammonium salt of 3-HP, and a mole concentration of the 3-HP was measured by using an UPLC (Maker: Waters, Column: ACQUITY UPLC™ EH C18, detection: UV 210 nm, amount of sample injected: 1 ml, flow rate of mobile phase solution: 0.200 ml/min, mobile phase solution: 0.1 mol phosphoric aqueous solution, an absolute examination method)

In particular, a titration method was as follows. The sample was added to a 500 ml-erlenmeyer flask, and a weight was measured. Then, 75 to 100 ml of distilled water was added to the flask. After adding 100 ml of more distilled water, 9 drops of a PP indicator was added to prepare an aqueous solution. Next, 0.5 N of NaOH was slowly added while mixing until the color of the aqueous solution is changed to faint pink. Then, 50 ml of 0.5 N NaOH was added, and mixed for 20 to 30 minutes. A free 3-HP acid (%) was calculated by using an equation of (ml of 0.5 N NaOH)×0.045×100/sample (g).

The results are shown in Table 1. About 96.91% of the ammonium salt of 3-HP was converted, and about 97.95% thereof was 3-HP. As a result, a yield of 3-HP was about 94.63%.

Also, as described above, 200 g of Sulfolane was added to the fermentation solution from which all water was removed, and then a temperature of the aqueous solution was increased to about 250° C. under a condition of about 300 ml/min of a $N_2$ flow rate, and allowed to react for 1 hour. The produce distilled out through an upper part of the 3-neck flask is cooled and collected. A mole concentration of an acrylic acid in the product was measured by using the UPLC.

The results are shown in Table 1. About 99.59% of the ammonium salt of 3-HP was converted, and about 50.4% thereof was acrylic acid. As a result, a yield of acrylic acid was about 50.19%.

TABLE 1

|  | Salt splitting | Dehydration |
| --- | --- | --- |
| Conversion (mol %) | 96.61 | 99.59 |
| Selectivity (mol %) | 97.95 | 50.4 |
| Yield (mol %) | 94.63 | 50.19 |

EXAMPLE 2

Preparation of Acrylic Acid from Ammonium Salt of 3-HP Included in Fermentation Solution in Continuous Reactor 65.1 g of a fermentation solution including 9.36 wt % of 3-HP was slowly injected to a 500 ml 3-neck flask containing 100 g of Sulfolane, which was heated to a temperature of 250° C., at a rate of 0.1 ml/min.

While the aqueous solution was allowed to react, $N_2$ was injected into the flask at a rate of 300 ml/min. The distilled out through an upper part of the 3-neck flask is cooled and collected. A mole concentration of an acrylic acid in the product was measured by using the UPLC.

About 94.2% of the ammonium salt of 3-HP was converted, and about 71.7% thereof was acrylic acid. As a result, a yield of acrylic acid was about 67.5%.

As described above, according to the one or more of the above embodiments of the present invention, a salt may be efficiently separated and/or an unsaturated acid may be efficiently produced by using a method of producing an unsaturated acid from an ammonium salt of a hydroxycarboxylic acid. Also, the method provides an efficient process that does not need an additional process to split the hydroxycarboxylic acid from a solvent.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing an unsaturated carboxylic acid from a salt of a hydroxycarboxylic acid, the method comprising:
   providing an aqueous solution comprising a salt of a hydroxycarboxylic acid;
   concentrating the aqueous solution by heating the aqueous solution to a first temperature to remove water, optionally under reduced pressure, wherein the first temperature is lower than a temperature needed to split a salt from the salt of the hydroxycarboxylic acid;
   adding a solvent with a boiling point of 200° C. or higher to the aqueous solution; and
   heating the aqueous solution at a temperature lower than the boiling point of the added solvent to split a salt from the salt of the hydroxycarboxylic acid while simultaneously dehydrating the hydroxycarboxylic acid, thereby converting the hydroxycarboxylic acid to an unsaturated carboxylic acid,
   wherein the step of heating the aqueous solution to a first temperature to remove water is performed before adding the solvent with a boiling point of 200° C. or higher.

2. The method of claim 1, wherein the solvent is a sulfur-containing compound or a nitrogen-containing compound.

3. The method of claim 1, wherein the solvent is Sulfolane.

4. The method of claim 1, wherein the solvent is a pyrrolidone.

5. The method of claim 4, wherein the pyrrolidone is N-methyl-2-pyrrolidone (NMP).

6. The method of claim 1, wherein the hydroxycarboxylic acid is selected from the group consisting of an alpha hydroxyl carboxylic acid, a beta hydroxycarboxylic acid, a gamma hydroxycarboxylic acid, an epsilon hydroxycarboxylic acid, and a combination thereof.

7. The method of claim 6, wherein the hydroxycarboxylic acid comprises an alpha hydroxycarboxylic acid, and the alpha hydroxycarboxylic acid is a lactic acid, a citric acid, a tartaric acid, or a glycolic acid.

8. The method of claim 6, wherein the hydroxycarboxylic acid comprises a beta hydroxycarboxylic acid, and the beta hydroxycarboxylic acid is a 3-hydroxypropionic acid, a 3-hydroxybutyric acid, a 3-hydroxyvaleric acid, a 3-hydroxyhexanoic acid, a 3-hydroxyheptanoic acid, or a 3-hydroxyoctanoic acid.

9. The method of claim 6, wherein the hydroxycarboxylic acid comprises a gamma hydroxycarboxylic acid, and the gamma hydroxycarboxylic acid is a 4-hydroxybutyric acid, 4-hydroxyvaleric acid, or 4-hydroxyhexanoic acid.

10. The method of claim 6, wherein the hydroxycarboxylic acid comprises an epsilon hydroxycarboxylic acid, and the epsilon hydroxycarboxylic is a 5-hydroxyvaleric acid or 5-hydroxyhexanoic acid.

11. The method of claim 1, wherein the salt is an ammonium salt.

12. The method of claim 1, wherein the salt is a quaternary ammonium salt.

13. The method of claim 1, wherein the heating the aqueous solution at a temperature lower than the boiling point of the added solvent comprises: heating the aqueous solution to a second temperature to split a salt from the salt of the hydroxycarboxylic acid; and
heating the salt-separated carboxylic acid to a third temperature, wherein the third temperature is equal to or lower than the boiling point of the solvent, and the second temperature is lower than the third temperature.

14. The method of claim 1, wherein heating the aqueous solution to first temperature to remove the water removes about 90 wt % or more of the water from the aqueous solution.

15. The method of claim 1, wherein the heating of the aqueous solution at a temperature lower than the boiling point of the solvent to split a salt from the salt of the hydroxycarboxylic acid converts 90% or more of salt to unsaturated hydroxycarboxylic acid.

16. The method of claim 1, wherein the aqueous solution comprising the salt of the hydroxycarboxylic acid is a cell culture solution comprising the salt of the hydroxycarboxylic acid.

17. The method of claim 1, wherein the aqueous solution comprising the salt of the hydroxycarboxylic acid is provided to a batch-oriented or continuous reactor before adding the solvent.

18. The method of claim 1, wherein the aqueous solution comprising the salt of the hydroxycarboxylic acid is provided to a batch-oriented or continuous fermenter before heating the aqueous solution to the first temperature.

* * * * *